(12) United States Patent
Scheiff et al.

(10) Patent No.: US 12,351,926 B2
(45) Date of Patent: Jul. 8, 2025

(54) PROCESS AND INTEGRATED PLANT FOR THE TREATMENT OF THE CARBON OXIDES FORMED IN THE PRODUCTION OF ALUMINUM

(71) Applicants: BASF SE, Ludwigshafen am Rhein (DE); thyssenkrupp AG, Essen (DE); thyssenkrupp Uhde GmbH, Dortmund (DE)

(72) Inventors: Frederik Scheiff, Ludwigshafen (DE); Marc Leduc, Ludwigshafen (DE); Andreas Bode, Ludwigshafen (DE); Karsten Bueker, Dortmund (DE); Nicolai Antweiler, Essen (DE)

(73) Assignees: BASF SE, Ludwigshafen am Rhein (DE); thyssenkrupp AG, Essen (DE); thyssenkrupp Uhde GmbH, Dortmund (DE)

( * ) Notice: Subject to any disclaimer, the term of this patent is extended or adjusted under 35 U.S.C. 154(b) by 706 days.

(21) Appl. No.: 17/596,027

(22) PCT Filed: May 28, 2020

(86) PCT No.: PCT/EP2020/064778
§ 371 (c)(1),
(2) Date: Dec. 2, 2021

(87) PCT Pub. No.: WO2020/245015
PCT Pub. Date: Dec. 10, 2020

(65) Prior Publication Data
US 2022/0349078 A1     Nov. 3, 2022

(30) Foreign Application Priority Data
Jun. 5, 2019  (EP) .................... 19178470

(51) Int. Cl.
*C25C 3/22*   (2006.01)
*C01B 3/38*   (2006.01)
*C01B 32/40*  (2017.01)
*C07C 1/12*   (2006.01)
*C07C 29/50*  (2006.01)
*C10K 3/02*   (2006.01)
*C25C 3/12*   (2006.01)

(52) U.S. Cl.
CPC ............... *C25C 3/22* (2013.01); *C01B 3/382* (2013.01); *C01B 32/40* (2017.08); *C07C 1/12* (2013.01); *C07C 29/50* (2013.01); *C10K 3/026* (2013.01); *C25C 3/125* (2013.01); *C01B 2203/0283* (2013.01); *C01B 2203/06* (2013.01); *C01B 2203/061* (2013.01)

(58) Field of Classification Search
CPC .. C25C 3/22; C01B 32/40; C07C 1/12; C10K 3/026
See application file for complete search history.

(56) References Cited

U.S. PATENT DOCUMENTS

| | | |
|---|---|---|
| 3,284,334 A | 11/1966 | Joseph et al. |
| 3,427,240 A | 2/1969 | Landrum et al. |
| 5,560,900 A | 10/1996 | Gbordzoe et al. |
| 7,238,215 B2 | 7/2007 | Gauthier et al. |
| 7,704,368 B2 | 4/2010 | Olah |
| 8,114,916 B2 | 2/2012 | Severinsky |
| 10,639,586 B2 | 5/2020 | Davidian et al. |
| 11,247,172 B2 | 2/2022 | Fulde |
| 2007/0264186 A1 | 11/2007 | Dybkjaer et al. |

FOREIGN PATENT DOCUMENTS

| | | |
|---|---|---|
| BE | 865319 A | 9/1978 |
| CA | 2579363 A1 | 3/2006 |
| CN | 1126698 A | 7/1996 |
| CN | 1482997 A | 3/2004 |
| CN | 101743343 A | 6/2010 |
| CN | 103059899 A | 4/2013 |
| CN | 105801354 A | 7/2016 |
| CN | 108290109 A | 7/2018 |
| DE | 19757148 A1 | 7/1999 |
| DE | 19845258 C1 | 3/2000 |
| DE | 102013102969 A1 | 9/2014 |
| EP | 2360296 A1 | 8/2011 |
| EP | 2660358 A2 | 11/2013 |

(Continued)

OTHER PUBLICATIONS

Aarhaug, et al., "A Study of Anode Baking Gas Composition", TMS Annual Meeting & Exhibition, 2018, pp. 1379-1385.
Aarhaug, et al., "Aluminium Primary Production Off-Gas Composition and Emissions: An Overview", JOM, vol. 71, Issue 9, Feb. 19. 2019, pp. 2966-2977.
European Search Report for EP Patent Application No. 19178470.1, Issued on Dec. 18, 2019, 3 pages.

(Continued)

*Primary Examiner* — Stuart L Hendrickson
(74) *Attorney, Agent, or Firm* — Grüneberg and Myers PLLC (57) ABSTRACT

A process can be used for the treatment of an offgas stream, which is formed in a plant for the production of aluminum by electrolytic reduction of aluminum oxide in a melt, using at least one anode composed of a carbon-containing material. The offgas stream contains carbon oxides due to the reduction of the aluminum oxide by the carbon. At least a substream of the carbon oxides contained in the offgas stream is reacted with hydrogen or mixed with a hydrogen stream and is subsequently passed to a use. After purification and conditioning of the offgas stream in a device, an enrichment, for example with carbon monoxide, can subsequently be carried out in a reactor and the synthesis gas obtained in this way can be fed to a chemical or biotechnological plant for the synthesis of chemicals of value.

20 Claims, 2 Drawing Sheets

(56) References Cited

FOREIGN PATENT DOCUMENTS

RU         2625152 C1    7/2017
WO   WO-2018/069504 A1  4/2018

OTHER PUBLICATIONS

International Search Report for PCT Patent Application No. PCT/EP2020/064778, Issued on Jul. 21, 2020, with English translation, 5 pages.
Written Opinion for PCT Patent Application No. PCT/EP2020/064778, Issued on Jul. 21, 2020, with English translation, 8 pages.
Brazilian Office Action issued in Patent Application No. BR112021024499-9 on Oct. 22, 2024, 8 pages (with English translation).

PROCESS AND INTEGRATED PLANT FOR THE TREATMENT OF THE CARBON OXIDES FORMED IN THE PRODUCTION OF ALUMINUM

CROSS-REFERENCE TO RELATED APPLICATIONS

This application is the National Stage entry under § 371 of International Application No. PCT/EP2020/064778, filed on May 28, 2020, and which claims the benefit of priority to European Application No. 19178470.1, filed on Jun. 5, 2019. The content of each of these applications is hereby incorporated by reference in its entirety.

BACKGROUND OF THE INVENTION

Field of the Invention

The present invention relates to a process for the treatment of an offgas stream which is obtained in a plant for the production of aluminum by electrolytic reduction of aluminum oxide in the melt using at least one anode composed of a carbon-comprising material and which owing to the reduction of the aluminum oxide by means of the carbon comprises carbon oxides. The present invention also relates to an integrated plant comprising an electrolysis apparatus for the production of aluminum by melt-electrolytic reduction of aluminum oxide, at least one apparatus for heat transfer in which at least a first substream of the offgas stream comprising carbon oxides from the plant for producing aluminum is cooled to a lower temperature and also a device for purification and/or conditioning of the offgas stream from the plant for producing aluminum.

Description of Related Art

The production of aluminum is carried out predominantly by melt flux electrolysis in the Hall-Heroult process. In this process, a eutectic mixture of the low-melting aluminum mineral cryolite ($Na_3[AlF_6]$) and the high-melting aluminum oxide (alumina) is subjected to melt flux electrolysis, with the aluminum oxide being reduced. In the melt, alumina oxide is present in dissociated form as its ions.

$Al_2O_3 \rightarrow 2Al^{3+} + 3O^{2-}$

The aluminum ions present in the melt migrate to the cathode where they take up electrons and are reduced to aluminum atoms.

$Al^{3+} + 3e^- \rightarrow Al$

The negative oxygen ions $O^{2+}$ migrate to the anode, release excess electrons and react with the carbon of the anode to form carbon monoxide and carbon dioxide which are given off as gases.

$C + 2O^{2-} \rightarrow CO_2 + 4e^-$

The overall reaction equation for the Hall-Heroult process is thus as follows:

$$2\,Al_2O_3 + 3C \rightarrow 4Al + 3CO_2 \quad (1)$$

Large amounts of carbon dioxide ($CO_2$) and carbon monoxide (CO) are formed in the reduction of aluminum oxide to aluminum. Apart from these two gases, sulfur dioxide ($SO_2$) and hydrogen fluoride (HF) are emitted. Carbon tetrafluoride ($CF_4$), hexafluoroethane ($C_2F_6$), sulfur hexafluoride ($SF_6$) and silicon tetrafluoride ($SiF_4$) are likewise relevant in terms of amount at low oxygen concentrations. The components $CO_2$, CO and $SO_2$ result from burning of the anode. The calcined petroleum coke which is used and comes from the processing of crude oil to give fuels contains proportions of sulfur, depending on quality in the range of, for example, from 1 to 7% by weight. In many cases, the offgases from aluminum production are released into the atmosphere [Aarhaug et al., "Aluminium Primary Production Off-Gas Composition and Emissions: An Overview", JOM, Vol. 71, No. 9, 2019]. In the emission of $SO_2$ and HF, particular permissible limit values must not be exceeded. In addition, the emissions of gases which are damaging to the climate are being increasingly regulated. About 70% of worldwide industrial energy consumption and 2.5% of the anthropogenic greenhouse gases are attributable to aluminum production. In the lifecycle of primary aluminum production, up to 20 kg of $CO_2$ equivalents can be formed per kg of aluminum. In Germany in the year 2018, the $CO_2$ emissions amounted to about one million metric tons of carbon dioxide equivalents (greenhouse gas emissions 2018 (VET_Bericht 2018). Perfluorinated hydrocarbons PFHCs) are formed as a result of an increased voltage which occurs when the proportion of dissolved aluminum oxide ($Al_2O_3$) is too low. Strategies for reducing the emissions from the Hall-Heroult process for producing aluminum are therefore of great economic and ecological interest.

Studies on the isolation and utilization of carbon dioxide comprised in the offgas stream from the melt flux electrolysis of aluminum oxide may be found in the literature. However, the comparatively low carbon dioxide concentrations in the offgas stream are critical to the economics of such utilization. The offgas stream is composed of the offgases from the melt flux electrolysis and ambient air. A known strategy for increasing the concentration is a reduction in the cell ventilation, but although this leads to a higher $CO_2$ concentration, it also results in a higher cell and offgas temperature.

EP 2 660 358 A2 describes a process for the electrolytic production of aluminum from aluminum oxide by the Hall-Heroult process, in which dust particles arising in the electrolysis cell and also offgases which comprise, in particular, hydrogen fluoride, sulfur dioxide and carbon dioxide are drawn off via an extraction channel and fed into a gas treatment apparatus. There, the offgases are brought into contact with an absorbent in the form of aluminum oxide which reacts with hydrogen fluoride and sulfur dioxide and the particles formed are separated off by means of a filter device. Dust particles entrained in the offgases are likewise separated off. Remaining sulfur dioxide can subsequently be separated off in a scrubbing apparatus by means of sea water or lime. Carbon dioxide can likewise be separated off by a scrubbing operation using an ammonium carbonate solution. Carbon dioxide which has been separated off is disposed of in this known process and the purified offgas is released into the environment. A heat exchanger is used to cool the offgas stream from the electrolysis apparatus, using ambient air or cooling water from a body of water as cooling medium. A substream of the offgases which have been cooled in this way can be recirculated to the electrolysis cell.

EP 2 360 296 A1 describes prior art similar to that described in the abovementioned document. It describes a process for the electrolytic production of aluminum, in which offgases from the electrolysis are drawn off, freed of dust and harmful gases and cooled; after purification and cooling a substream of the purified and cooled offgases is recirculated to the electrolysis cell. However, this known process does not provide for carbon oxides comprised in the offgases from the electrolysis cell to be passed to a use, in the sense that these gases serve as starting materials for a subsequent synthesis of chemicals of value. Rather, carbon dioxide is regarded as a waste product to be disposed of and is, after compression, stored in a disused mine.

DE 197 57 148 A1 likewise describes a process for producing aluminum by melt electrolysis from aluminum oxide, in which dust-like constituents and hydrogen fluoride are removed from the offgas by means of a getter material. This forms aluminum fluoride which can be recirculated to the melt. A work-up of the carbon oxides which are likewise present in the offgas from the melt electrolysis is not described in this document.

SUMMARY OF THE INVENTION

It is an object of the present invention to provide a process and an integrated plant of the type mentioned above, in which it becomes possible to pass carbon oxides formed in the electrolytic production of aluminum at least partly to an economically purposeful use.

A further object was to pass the offgases formed in the production of the anodes to a purposeful use.

The abovementioned object is achieved by a process of the type mentioned at the outset having the features as described and an integrated plant having the features as described.

DETAILED DESCRIPTION OF THE INVENTION

According to the invention, at least a substream of the carbon oxides comprised in the offgas stream is purified and/or conditioned and reacted with hydrogen and reduced to carbon monoxide and/or methane or is mixed with a hydrogen stream and subsequently passed to utilization in a chemical or biotechnological reaction.

In a preferred further development of the process of the invention, there are, in particular, three alternative possibilities. According to a first variant, the carbon oxides comprised in the offgas stream can be fed to a device in which a reverse water gas shift reaction is carried out; in this, at least part of the carbon dioxide is reacted with hydrogen and reduced to carbon monoxide so as to produce a synthesis gas stream.

In a narrow sense, the term "synthesis gas" refers to industrially produced gas mixtures comprising hydrogen and carbon monoxide together with further gases. Depending on the ratio in which hydrogen and carbon monoxide are comprised in the gas mixture, the synthesis gas can be used to produce various products, for example liquid fuels by the Fischer Tropsch process at a ratio of hydrogen to carbon monoxide of 1-2:1, alcohols such as methanol or ethanol at a ratio of about 2:1, or methane or synthetic natural gas (SNG) by a methanation at a ratio of about 3:1.

The water gas shift reaction is usually used to reduce the proportion of carbon monoxide in synthesis gas and to produce further hydrogen. This occurs according to the following reaction equation:

$$CO+H_2O \rightarrow CO_2+H_2 \qquad (2)$$

The abovementioned reaction (2) is an equilibrium reaction which proceeds in the reverse direction under changed reaction conditions, for example when the temperature is increased. This reverse reaction will in this text be referred to as reverse water gas shift reaction and corresponds to the reaction equation below:

$$CO_2+H_2 \rightarrow CO+H_2O \qquad (3)$$

In a preferred further development of the process of the invention, the abovementioned reaction (3) can thus be utilized for converting part of the carbon dioxide formed in the melt flux electrolysis of aluminum oxide into carbon monoxide by means of hydrogen, which is, for example, obtained by pyrolysis of hydrocarbons or originates from another source, in order to produce further carbon monoxide in this way and provide a synthesis gas which has a higher proportion of carbon monoxide combined with a reduced content of carbon dioxide, so that this synthesis gas mixture has a composition which is particularly suitable for specific further reactions.

When, for example, the ratio of carbon monoxide to carbon dioxide in the synthesis gas mixture is comparatively high, the synthesis gas mixture can, according to a preferred variant of the present invention, be utilized, for example, together with hydrogen in a chemical or biotechnological plant.

In a second preferred variant of the process of the invention, a Sabatier reaction in which carbon dioxide and/or carbon monoxide is converted by reaction with hydrogen into methane is carried out in a device. The reaction of carbon monoxide with hydrogen in this reaction named after the French chemist Paul Sabatier occurs according to the reaction equation below:

$$CO+3H_2 \rightarrow CH_4+H_2O \qquad (4)$$

In a similar way, carbon dioxide can be reacted with hydrogen according to the reaction equation below:

$$CO_2+4H_2 \rightarrow CH_4+2H_2O \qquad (5)$$

The methane obtained in this way can either serve as energy carrier and, for example, be stored or else be utilized as starting material in a chemical or biotechnological plant for the synthesis of other chemical products of value.

In a third preferred variant of the invention, the carbon oxides comprised in the offgas stream are fed to a device in which they are mixed with a hydrogen stream. Such a mixture then comprises, for example, carbon monoxide and hydrogen and likewise forms a synthesis gas which can be utilized as feed gas stream in a chemical or biotechnological plant.

A preferred further development of the process of the invention provides for at least a substream of offgases from the plant for producing aluminum firstly to be fed into a first device for purification and/or conditioning of the offgas before the offgas stream is fed to the device in which the reverse water gas shift reaction or the Sabatier reaction is carried out or the offgas is mixed with hydrogen. In such a device, the removal, for example, of gas constituents of the offgas from the plant for producing aluminum which interfere in the further reaction or are environmentally damaging, for example hydrogen fluoride or sulfur dioxide, can be carried out. In this device, gaseous constituents can, for example, be scrubbed out of the offgas or solid particles can be removed by filtration or adsorption. However, for example, gases can also be added in this device when variation of the composition of the offgas mixture is advantageous for the subsequent reaction process for producing chemical products of value.

According to a first possibility within the framework of a preferred further development of the invention, at least a substream, for example a second substream of the offgas stream, is, after leaving the plant for producing aluminum, firstly cooled to a lower temperature in an apparatus for heat exchange and only then is fed to the abovementioned device for purification and/or conditioning of the offgas. This cooling can, for example, occur for heat transfer in a heat exchanger so that the energy comprised in the hot offgases can, for example, be utilized in other parts of the plant for heating a stream of material.

As an alternative thereto or in addition, at least one substream, in the case of the above-described variant optionally a first substream, of the offgases from the plant for producing aluminum can be fed without prior cooling to the device for purification and/or conditioning of the offgas. The offgas stream can thus also be divided and one substream of the offgas stream can firstly be cooled and a further substream of the offgas stream can be used further without cooling. As an alternative, the entire offgas stream can also be used uncooled or the entire offgas stream can be cooled before further processing.

A preferred further development of the invention provides for at least a first substream of the offgas stream comprising carbon oxides from the plant for producing aluminum to be recirculated to this plant.

This substream of the offgas which is recirculated to the plant can be an offgas stream which has previously been cooled to a lower temperature in an apparatus for heat exchange. This measure has the advantage that the constituents of the offgas stream which result from the ambient air are replaced by recirculation of the offgas stream from the reduction cell and the two components carbon dioxide and carbon monoxide thus accumulate in the offgas stream from the electrolysis cell.

Significant constituents of the offgas stream from the electrolysis cell in the melt flux electrolysis of aluminum oxide are the components carbon dioxide and carbon monoxide which result from the burning of the anodes made of carbon. The anodes consist of calcined petroleum coke or pyrolysis carbon and also generally pitch as binder and are, for example, baked in shaft furnaces or rotary tube furnaces with usage of energy. The finished anodes are used in the Hall-Heroult electrolysis for the production of aluminum using cryolites and energy. The offgases from the reduction cell result essentially from the electrolytic reduction of the aluminum oxide to aluminum according to the above reaction equation (1), and also from the reoxidation of aluminum according to the equation (6) below:

$$2Al + 3CO_2 \rightarrow Al_2O_3 + 3CO \quad (6)$$

of the Boudouard reaction between primary $CO_2$ gases and anode carbon according to the reaction equation (7) below:

$$CO_2 + C \rightarrow 2CO \quad (7)$$

and significant burning of the anodes in the presence of the atmospheric oxygen above the electrolytic bath according to the reaction equation (8) below:

$$C + O_2 \rightarrow CO_2 \quad (8)$$

In the steady state, the following division of anode carbon consumption is obtained, by way of example:

| Mechanism | Anode consumption, % by weight |
|---|---|
| $2 Al_2O_3 + 3 C \rightarrow 4 Al + 3 CO_2$ | 66-76 |
| $C + O_2 \rightarrow CO_2$ and $2 C + O_2 \rightarrow 2 CO$ | 8-15 |
| $CO_2 + C \rightarrow 2 CO$ | 5-6 |
| Dust | 0.3 |
| $2 Al + 3 CO_2 \rightarrow Al_2O_3 + 3 CO$ | 7-8 |
| Pyrolysis | 0.2 |
| Sulfur, metallic impurities and recycled anode residues | 3.5-4.5 |
| Nett carbon consumption/ kg of C/t of Al | 400-450 |

The burning of the anodes in the presence of atmospheric oxygen brings about, at a carbon consumption of from about 8% by weight to about 15% by weight, a significant proportion of the total consumption. Furthermore, removal of the greenhouse gases is costly due to dilution of the offgases formed with ambient air. According to the present invention, partial recycling of the offgas stream is preferably proposed. The reaction of $CO_2$ and CO with the carbon of the anode is greatly kinetically limited at the prevailing resonance times of the gas phase. The consequence is a greatly reduced burning of the anodes and concentration of the components $CO_2$ and CO in the offgas stream from the reduction cell. The offgas stream is therefore preferably cooled to a lower temperature in a heat exchanger and partly recirculated. Part of the offgas stream can, for example, either be used further after cooling or be transferred without cooling to the next part of the plant, depending on the type of further utilization which is intended. Depending on the composition of the offgas stream, purification and conditioning may then be required.

Particularly when an integrated plant comprising plant regions in which a hydrocarbon pyrolysis, for example a methane pyrolysis for producing anodes, is carried out and plant regions in which the melt flux electrolysis for the production of aluminum is carried out is created, the carbon oxides formed in aluminum production and optionally the offgases formed in anode production can usefully be utilized in the close vicinity of the place in which they arise.

In a preferred further development of the process of the invention, a synthesis gas stream obtained from the offgas stream from the electrolysis cell is preferably used for the production of methanol, at least one alcohol and/or at least one other chemical product of value. For the purposes of the present invention, other chemical products of value are organic compounds based on carbon of effectively any type which can be produced from synthesis gases, for example olefins, aldehydes, ethers, etc., by means of production processes known per se, or else fuels or fuel mixtures such as gasoline or diesel or energy-rich gases such as methane or other higher gaseous or liquid hydrocarbons and the like.

It has been mentioned above that the hydrogen supplied to the reverse water gas shift reaction or the Sabatier reaction or to mixing with the carbon oxides from the offgas can be produced, for example, by pyrolysis of hydrocarbons, in particular methane or natural gases. A further advantage of this variant of the process is that the pyrolysis carbon which is likewise formed in the pyrolysis of hydrocarbons, in particular methane or natural gas, can be used for producing anodes for the electrolytic production of aluminum. A particular advantage of the pyrolysis carbon compared to conventional calcined petroleum coke is that virtually no sulfur is present and the sulfur emissions are thus drastically reduced.

When, according to a preferred variant of the process, cooling of at least a substream of the offgases is provided, this gives the further advantage that a methane-comprising gas stream, in particular a feed gas stream which is used for the pyrolysis of the hydrocarbon, in particular of methane or natural gas, can simultaneously be heated by the offgas stream in the apparatus for heat exchange, so that the energy comprised in the offgas can be utilized in the process at this point.

One possible variant of the process of the invention provides for the offgas stream comprising carbon dioxide and carbon monoxide which is obtained after purification and conditioning to be directly utilized chemically. As an alternative thereto, hydrogen is mixed into the offgas stream before chemical utilization of the gas mixture is carried out. In another alternative, the abovementioned reverse water gas shift reaction can firstly be used to increase the proportion of carbon monoxide and the synthesis gas stream then obtained can be converted in a chemical or biotechnological plant into chemical products such as methanol, higher alcohols or other chemical products of value. In a further alternative variant of the process, part or all of the carbon monoxide and/or part or all of the carbon dioxide can be converted into methane in a Sabatier reaction.

The present invention further provides an integrated plant comprising an electrolysis apparatus for the production of aluminum by melt-electrolytic reduction of aluminum oxide using at least one anode composed of a carbon-comprising material, at least one apparatus for heat exchange in which at least a substream of the offgas stream comprising carbon oxides from the plant for producing aluminum is cooled to a lower temperature and also at least one device for purification and/or conditioning of the offgas stream from the plant for producing aluminum, wherein the integrated plant further comprises, according to the invention, at least one reactor for reaction of the offgas stream with hydrogen to form synthesis gas and/or to form methane and/or an apparatus for mixing the offgas stream with hydrogen for subsequent utilization in a chemical or biotechnological plant to produce methanol, at least one alcohol and/or at least one other chemical product of value.

Such a plant concept has the advantage that the offgas stream from the melt electrolysis of aluminum oxide can be utilized in many ways within a complex of a number of plant parts of a plant. Firstly, for example, a synthesis gas or a methane-comprising gas mixture which is suitable for the production of chemical products of value is produced from carbon oxides comprised in the offgas. In addition, the heat comprised in the offgas stream can be utilized for heat exchange in which a feed gas stream for the pyrolysis of hydrocarbons is preheated, with this pyrolysis in turn producing hydrogen which can be mixed into the synthesis gas or be used for the Sabatier reaction. Furthermore, the pyrolysis carbon from the pyrolysis of hydrocarbons can be utilized within the integrated plant for production of the anodes for the melt flux electrolysis.

The volatile hydrocarbons formed in the production of the anode (see, for example, Aarhaug et al., "A Study of Anode Baking Gas Composition", Light Metals 2018, pp. 1379-1385), in particular methane, benzene and polycyclic aromatics, can advantageously be recirculated to the reactor for hydrocarbon pyrolysis. For example, these volatile hydrocarbons are conveyed via a conduit (27) from the apparatus for anode production (1) into the reactor for hydrocarbon pyrolysis (21) or these volatile hydrocarbons are introduced via a conduit (27) into the feed conduit (22) for methane or other hydrocarbons to the reactor for hydrocarbon pyrolysis (21).

Any perfluorinated hydrocarbons, PFHCs, present in the anode offgas are converted into hydrogen fluoride in the methane pyrolysis. The hydrogen fluoride is advantageously removed from the gas stream, for example adsorbed/absorbed with the aid of $Al_2O_3$ or $Al(OH)_3$. The fluoride-laden absorbent is advantageously added to the cryolite melt and the fluoride is thus recycled.

The integrated plant of the invention preferably further comprises a device to which the carbon oxides comprised in the offgas stream are fed and in which a reverse water gas shift reaction in which at least part of the carbon dioxide is reacted with hydrogen and reduced to carbon monoxide so as to produce a synthesis gas stream is carried out or in which a Sabatier reaction in which carbon dioxide and/or carbon monoxide is converted into methane by reaction with hydrogen is carried out or in which the carbon oxides comprised in the offgas stream are mixed with a hydrogen stream.

In addition, the integrated plant of the invention preferably further comprises at least two independent conduits, where a first offgas stream which has been cooled in the apparatus for heat exchange can be conveyed by means of the first conduit and, independently thereof, a second uncooled offgas stream can be conveyed directly from the plant for producing aluminum into the device for purification and/or conditioning by means of the second conduit. This possible structural variant of the integrated plant of the invention creates the possibility of utilizing the heat energy comprised in the offgas stream only partly in the heat exchange for heating another feed gas stream, whereas the heat energy comprised in the uncooled substream of the offgas which is, optionally after purification and conditioning, used directly for producing a synthesis gas mixture or methane-comprising gas mixture can be utilized in the further synthesis and utilization process.

Figure 1:
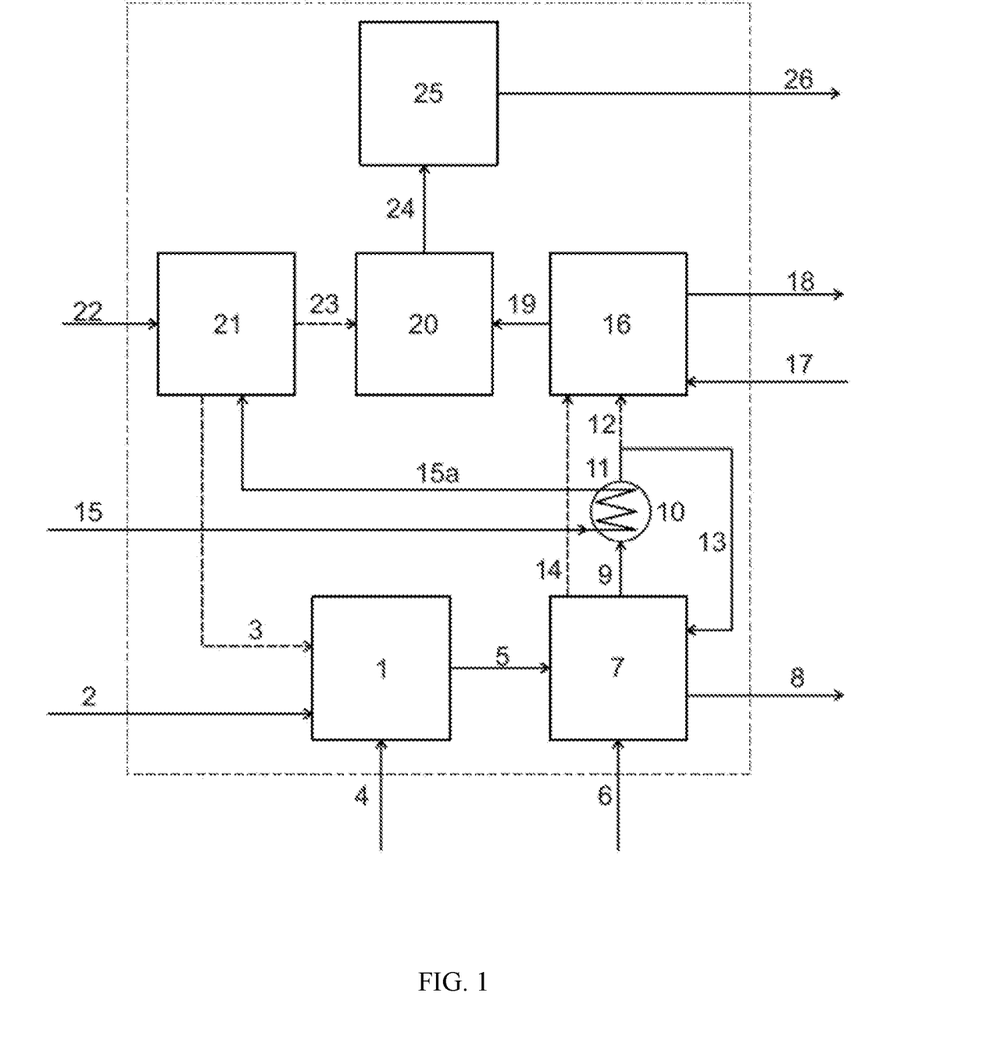
FIG. 1 shows a simplified plant flow diagram of a plant according to the invention for treatment of an offgas stream formed in the production of aluminum by electrolytic reduction of aluminum oxide in the melt.
Figure 2:
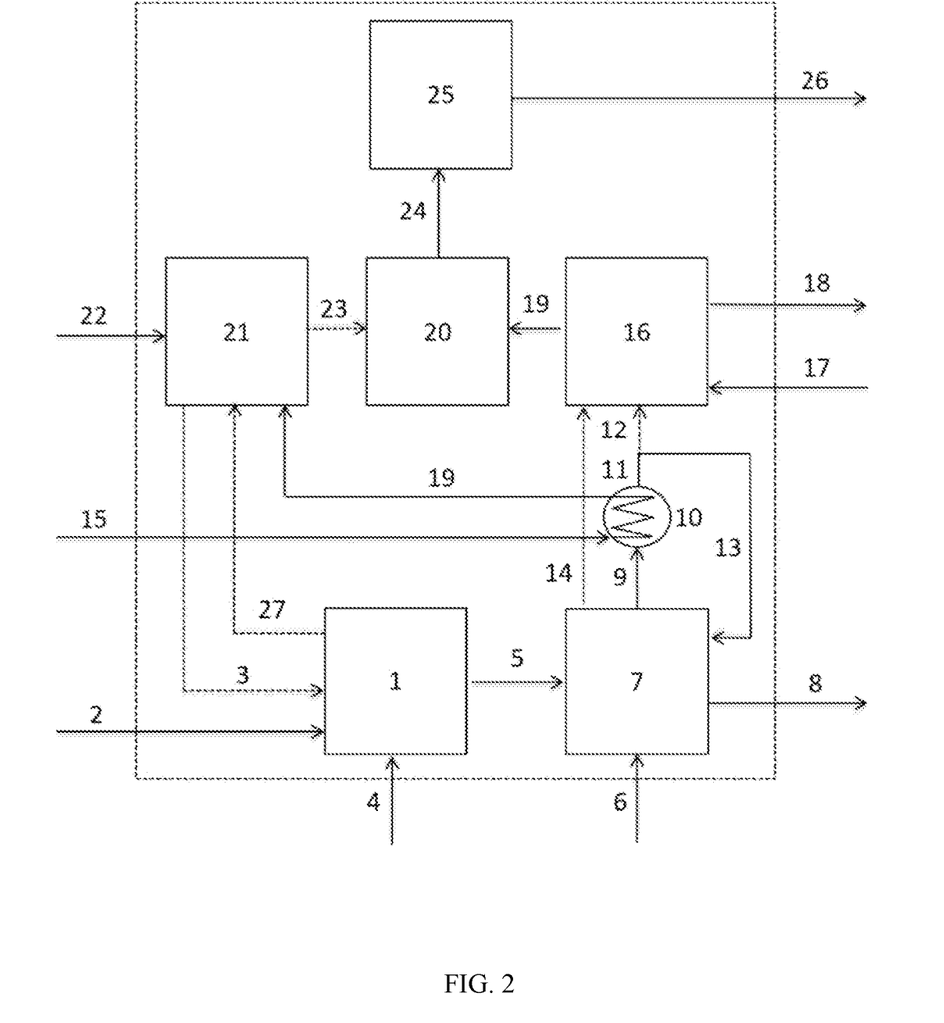
FIG. 2 shows another simplified plant flow diagram of a plant according to the invention for treatment of an offgas stream formed in the production of aluminum by electrolytic reduction of aluminum oxide in the melt.

The present invention will be illustrated below with the aid of working examples with reference to the accompanying drawing, In the drawing:

FIGS. 1 and 2 show a simplified plant flow diagram of a plant according to the invention for treatment of an offgas stream formed in the production of aluminum by electrolytic reduction of aluminum oxide in the melt.

Reference is made in the following to FIGS. 1 and 2 and an illustrative embodiment of the process of the invention and also an integrated plant which can be used in the process will be explained in more detail with the aid of this schematic simplified depiction. Only the essential plant components of such an integrated plant are shown by way of example in the drawing. The integrated plant comprises a hydrogen source, in particular a pyrolysis reactor 21 in which pyrolysis of hydrocarbons, for example of methane, is carried out. For this purpose, methane is fed via a feed conduit 15 to this pyrolysis reactor 21 or a more complex apparatus comprising such a pyrolysis reactor and energy is supplied via a device 22 to the reactor 21 in order to bring the methane to the temperature of, for example, more than 800° C. required for the pyrolysis. Hydrogen and pyrolysis carbon are formed in the pyrolysis reactor 21 by the pyrolytic decomposition. The hydrogen is conveyed from the reactor 21 via the conduit 23 to a further reactor 20 in which, for example, a reverse of water gas shift reaction or a Sabatier reaction takes place, as will be explained in more detail below. The pyrolysis carbon produced in the pyrolysis reactor 21 is fed via a feed device 3 to an apparatus 1 in which anodes for the melt electrolysis 7 by the Hall-Heroult process are produced from the pyrolysis carbon. It would in principle be possible to produce anodes from pure pyrolysis carbon. However, calcined petroleum coke mixtures are preferably used, pyrolysis carbon is mixed into the petroleum coke and this mixture is then pressed after addition of pitch to form anodes which are then baked. The volatile hydrocarbons formed in the production of the anode are recirculated via a conduit 27 to the pyrolysis reactor 21.

A binder, for example pitch, is fed to the abovementioned apparatus 1, which can be, for example, a shaft furnace or rotary tube furnace, via a further feed device 2 and the electrodes (anodes) produced in this way in the apparatus 1 are then conveyed via a further feed device 5 from the apparatus 1 to the plant 7 in which the melt flux electrolysis of aluminum oxide occurs. The further starting materials which are necessary for the melt flux electrolysis, namely the aluminum oxide, cryolite, which is used for lowering the melting point of the solids to be melted, and energy which is necessary to bring this mixture of solids to the melting temperature of the eutectic, which is generally above 950° C., are supplied via various feed devices 6, which are here represented, schematically simplified, by only a single line. Aluminum is then formed as product in this plant 7 and can be discharged from the plant via the discharge device 8. Furthermore, a gas mixture of carbon dioxide and carbon monoxide in a ratio which depends on various parameters in the electrolysis of the aluminum oxide is formed by oxidation of the anodes consisting of pyrolytic carbon in the plant 7. This gas mixture can, for example, be discharged from the plant 7 via a first conduit 9 and be fed to a heat exchanger 10 in which cooling of the gas mixture occurs. The heat exchange occurs by exchange with the methane or natural gas which is supplied via the conduit 15, is preheated in this way and is then fed via the conduit 15a to the pyrolysis reactor 21. The cooled offgases then go into the conduit 11. This can be considered to be an example of energy integration in an integrated plant according to the invention, but there are also alternative possibilities here.

Downstream of the heat exchanger 10, the gas stream 11 is then divided, with a first substream being fed via the conduit 12 depicted as a broken line to the device 16 for purification and conditioning of the offgases. A second substream of the cooled offgas is in contrast recirculated via the conduit 13 to the plant 7 in which the melt flux electrolysis of aluminum oxide takes place, as a result of which the offgases in the electrolysis cell become enriched with carbon oxides.

After the offgas stream has been purified and conditioned in the device 16, the gas mixture is fed via the conduit 19 to a reactor 20 in which a reverse water gas shift reaction or, for example, a Sabatier reaction can be carried out. In the simplest case, the plant part designated by 20 can, as an alternative, also be only a mixing apparatus in which the gas stream from the conduit 19, which comprises carbon oxides, is mixed with hydrogen from the conduit 23.

The reverse water gas shift reaction which is by way of example carried out in the reactor 20 and proceeds according to the above reaction equation (3) serves to decrease the proportion of carbon dioxide in the gas mixture and to increase the proportion of carbon monoxide in the gas mixture. For this purpose, hydrogen is fed via the conduit 23 to the reactor 20 so as to react with the gas mixture from the plant 7 for melt electrolysis, with the gas mixture comprising carbon oxides being fed to the reactor 20 via the conduit 19 which connects the device 16 for purification and conditioning of the offgases to the reactor 20. A gas mixture which comprises, inter alia, carbon monoxide and hydrogen and is thus suitable as synthesis gas is formed in the apparatus 20. This synthesis gas is fed via the conduit 24 to a chemical or biotechnological plant 25 in which chemicals of value such as methanol, higher alcohols or the like can be synthesized by methods which are known per se. The product obtained in this way can be discharged from the plant 25 via the conduit 26.

As an alternative thereto, a Sabatier reaction, for example, in which carbon dioxide and/or carbon monoxide comprised in the gas stream supplied from the conduit 19 is reacted with hydrogen to form methane can also be carried out in the reactor. The hydrogen which is supplied via the conduit 23 to the reactor 20 is used for this purpose. The methane produced in this way can either be fed via the conduit 24 to a chemical or biotechnological plant 25 and there be processed further as described above or can optionally be discharged and stored.

A third possible alternative is for the plant 20 to be a simple mixing apparatus to which the gas stream from the conduit 19, which comprises carbon oxides from the offgas, and hydrogen via the conduit 23 are supplied in order to obtain a gas mixture which is again suitable for further syntheses of chemicals of value, for example organic compounds, in the chemical or biotechnological plant 25.

In an alternative variant of the invention, the heat exchanger 10 is circumvented and the offgases from the melt electrolysis are in their entirety or only a substream thereof are conveyed from the plant 7 via the conduit 14 depicted as a broken line in FIG. 1 directly and thus uncooled to the device 16 for purification and conditioning. Various purification processes can take place in this device and in addition various streams can be fed via the conduit 17 to the device 16 in order to purify the offgas stream from the melt electrolysis 7, i.e. to remove undesirable constituents, for example by means of scrubbing operations and/or by means of filter devices. Furthermore, streams such as additional gases can also be fed in via the conduit 17 in order to change the composition of the gas mixture in the device 16 in a targeted manner, so that an altered composition which leads to a gas mixture advantageous for subsequent reactions and synthesis steps in the reactor 20 and/or in the chemical or biotechnological plant 25 is obtained. Constituents which are removed from the offgas stream in the device 16 can be discharged from the device 16 via the conduit 18.

LIST OF REFERENCE NUMERALS

1 Shaft furnace or rotary furnace
2 Feed device for pitch and optionally petroleum cokes or other carbon sources
3 Feed device for pyrolysis carbon
4 Device for introduction of energy
5 Feed device for anodes
6 Device for introduction of energy
7 Melt electrolysis of aluminum oxide
8 Discharge of aluminum
9 Offgas stream
10 Apparatus for heat exchange
11 Offgas stream
12 Offgas stream
13 Recirculated offgas stream
14 Uncooled offgas stream
15 Methane fed in 15a Conduit for preheated methane
16 Device for purification and conditioning
17 Input
18 Output
19 Gas stream comprising carbon oxides
20 Reverse water gas shift reaction
21 Hydrocarbon pyrolysis, pyrolysis reactor
22 Feed device for energy
23 Conduit for hydrogen
24 Synthesis gas mixture
25 Chemical or biotechnological plant
26 Discharge conduit for product
27 Conduit for volatile hydrocarbons

The invention claimed is:

1. A process for the treatment of an offgas stream comprising carbon oxides, the process comprising:
   purifying and/or conditioning at least a substream of the offgas stream comprising carbon oxides, to produce a gas stream comprising carbon oxides,
   reacting the gas stream comprising carbon oxides with hydrogen and reducing carbon oxides to carbon monoxide and/or methane, to produce a synthesis gas stream; or mixing the gas stream comprising carbon oxides with a hydrogen stream, to produce a mixed stream composed of carbon oxides and hydrogen, and
   subsequently passing the synthesis gas stream or the mixed stream composed of carbon oxides and hydrogen to utilization in a chemical or biotechnological reaction;
   wherein the offgas stream comprising carbon oxides is formed in a plant for producing aluminum by electrolytic reduction of aluminum oxide in a melt using at least one anode composed of a carbon-comprising material,
   wherein the offgas stream comprises the carbon oxides due to the electrolytic reduction of the aluminum oxide by carbon, and
   wherein pyrolysis carbon formed in the pyrolysis of hydrocarbons is used for producing an anode for the electrolytic production of aluminum,
   wherein said pyrolysis carbon is mixed with a binder and optionally petroleum coke or other carbon sources and then baked to form an anode.

2. The process according to claim 1, wherein the gas stream comprising carbon oxides is fed to a device in which a reverse water gas shift reaction is carried out, in which at least part of the carbon oxides are reacted with the hydrogen and reduced to the carbon monoxide, to produce the synthesis gas stream.

3. The process according to claim 1, wherein the gas stream comprising carbon oxides is fed to a device in which a Sabatier reaction is carried out, in which carbon dioxide and/or carbon monoxide is converted into the methane by reaction with the hydrogen.

4. The process according to claim 1, wherein the gas stream comprising carbon oxides is fed to a device in which the gas stream comprising carbon oxides is mixed with the hydrogen stream.

5. The process according to claim 1, wherein at least a substream of offgases from the plant for producing aluminum is fed without prior cooling to a device for purification and/or conditioning of offgas.

6. The process according to claim 1, wherein the at least a substream of the offgas stream is firstly cooled to a lower temperature in an apparatus for heat exchange after leaving the plant for producing aluminum, and is then fed to a device for purification and/or conditioning of offgas.

7. The process according to claim 1, wherein at least a further substream of the offgas stream comprising carbon oxides is recirculated to the plant for producing aluminum.

8. The process according to claim 7, wherein the offgas stream comprising carbon oxides is firstly cooled to a lower temperature in an apparatus for heat exchange after leaving the plant for producing aluminum, to produce a cooled offgas stream, and
   wherein the at least a further substream of the cooled offgas stream is recirculated to the plant for producing aluminum.

9. The process according to claim 1, wherein the offgas stream comprising carbon oxides is firstly cooled to a lower temperature in an apparatus for heat exchange, to produce a cooled offgas stream, and
   wherein the cooled offgas stream is then divided into at least two substreams, wherein one of the at least two substreams is fed to a device for purification and/or conditioning of offgas while a further substream of the at least two substreams is recirculated to the plant for producing aluminum.

10. The process according to claim 1, wherein the synthesis gas stream, the mixed stream composed of carbon oxides and hydrogen, or a methane-comprising gas stream is subsequently fed to a chemical or biotechnological plant.

11. The process according to claim 10, wherein the synthesis gas stream, the mixed stream composed of carbon oxides and hydrogen, or the methane-comprising gas stream is used in the chemical or biotechnological plant in order to produce methanol, at least one alcohol, and/or at least one other chemical product of value.

12. The process according to claim 1, wherein the hydrogen is fed to a device for the production of the synthesis gas stream or for the production of the mixed stream composed of carbon oxides and hydrogen, and
   wherein the hydrogen is produced by pyrolysis of hydrocarbons.

13. The process according to claim 12, wherein pyrolysis carbon formed in the pyrolysis of hydrocarbons is used for producing anodes for electrolytic production of aluminum.

14. The process according to claim 1, wherein a methane-comprising gas stream is heated by the offgas stream comprising carbon oxides in an apparatus for heat exchange.

15. The process according to claim 13, wherein volatile hydrocarbons formed in the production of an anode are recirculated via a conduit to a reactor for the pyrolysis of hydrocarbons.

16. The process according to claim 12, wherein the hydrogen fed to the device is produced by pyrolysis of methane or natural gas.

17. The process according to claim 1, wherein said pyrolysis carbon is mixed with a binder and optionally petroleum coke or other carbon sources, pressed to form an anode and then baked.

18. The process according to claim 1, wherein said pyrolysis carbon is mixed with a binder and petroleum coke, pressed to form an anode and then baked.

19. A process for the treatment of an offgas stream comprising carbon oxides, the process comprising:
   purifying and/or conditioning at least a substream of the offgas stream comprising carbon oxides, to produce a gas stream comprising carbon oxides,
   reacting the gas stream comprising carbon oxides with hydrogen and reducing carbon oxides to carbon monoxide and/or methane, to produce a synthesis gas stream; or mixing the gas stream comprising carbon oxides with a hydrogen stream, to produce a mixed stream composed of carbon oxides and hydrogen, and subsequently passing the synthesis gas stream or the mixed stream composed of carbon oxides and hydrogen to utilization in a chemical or biotechnological reaction;

wherein the offgas stream comprising carbon oxides is formed in a plant for producing aluminum by electrolytic reduction of aluminum oxide in a melt using at least one anode composed of a carbon-comprising material, wherein the offgas stream comprises the carbon oxides due to the electrolytic reduction of the aluminum oxide by carbon, and wherein at least a further substream of the offgas stream comprising carbon oxides is recirculated to the plant for producing aluminum.

20. An integrated plant, comprising:

an electrolysis apparatus for production of aluminum by melt-electrolytic reduction of aluminum oxide, using at least one anode composed of a carbon-comprising material, at least one device for purification and/or conditioning of an offgas stream from the electrolysis apparatus, and at least one reactor for reaction of the offgas stream with hydrogen to form a synthesis gas and/or to form methane, and/or an apparatus for mixing the offgas stream with hydrogen; for subsequent utilization in a chemical or biotechnological plant to produce methanol, at least one alcohol, and/or at least one other chemical product of value, wherein the integrated plant comprises at least two independent conduits, and wherein a first offgas stream which has been cooled in an apparatus for heat exchange can be conveyed by the first conduit and, independently thereof, a second uncooled offgas stream can be conveyed directly from the electrolysis apparatus into the at least one device for purification and/or conditioning.

* * * * *